(12) United States Patent
Falloon et al.

(10) Patent No.: US 7,776,289 B2
(45) Date of Patent: Aug. 17, 2010

(54) METHOD AND APPARATUS FOR PRODUCING DECABROMODIPHENYL ALKANES

(75) Inventors: Stephen B Falloon, Lafayette, IN (US); Samuel U Mulligan, Camden, AR (US); Donavon M McElveen, Norphlet, AR (US); Ray W Atwell, West Lafayette, IN (US)

(73) Assignee: Chemtura Corporation, Middlebury, CT (US)

( * ) Notice: Subject to any disclaimer, the term of this patent is extended or adjusted under 35 U.S.C. 154(b) by 1296 days.

(21) Appl. No.: 11/026,624

(22) Filed: Dec. 30, 2004

(65) Prior Publication Data

US 2005/0118080 A1     Jun. 2, 2005

Related U.S. Application Data

(62) Division of application No. 10/323,012, filed on Dec. 18, 2002, now Pat. No. 6,841,707.

(60) Provisional application No. 60/345,063, filed on Dec. 21, 2001.

(51) Int. Cl.
*B01J 19/00* (2006.01)
*B01J 19/26* (2006.01)
*B01J 8/00* (2006.01)
*C07C 25/18* (2006.01)

(52) U.S. Cl. .................... 422/234; 422/211; 422/220; 570/206

(58) Field of Classification Search ................ None
See application file for complete search history.

(56) References Cited

U.S. PATENT DOCUMENTS

| 2,022,634 | A | 11/1935 | Britton et al. |
| 2,033,612 | A | 3/1936 | Clark et al. |

(Continued)

FOREIGN PATENT DOCUMENTS

EP     0299270 A1     1/1989

(Continued)

OTHER PUBLICATIONS

International Search Report from Corresponding International (PCT) Patent Application, Dated Apr. 22, 2003, 3 pages.

(Continued)

*Primary Examiner*—Jennifer A Leung
(74) *Attorney, Agent, or Firm*—Joseph Suhadolnik

(57) ABSTRACT

A method of producing decabromodiphenyl alkanes includes the steps of charging a reaction vessel with bromine and a bromination catalyst and introducing a diphenyl alkane into the vessel at a location above the level of the charge bromine and catalyst. A dip tube apparatus for introducing the diphenyl alkane includes an inner tube and an outer tube, each of which are disposed above the surface of the bromine reaction vessel. The inner tube is fitted with a plug having an opening. Diphenyl alkane flows through the inner tube, out the opening in the plug, and into the reactor. The outer tube is disposed around and along the inner tube. Reaction mass from the vessel is recirculated from the vessel, through the outer tube and back to the vessel so as to form a curtain of reaction mass around the stream of diphenyl alkane being simultaneously fed into the reaction vessel.

10 Claims, 2 Drawing Sheets

U.S. PATENT DOCUMENTS

| | | |
|---|---|---|
| 2,244,284 A | 6/1941 | Britton et al. |
| 2,607,802 A | 8/1952 | Britton et al. |
| 2,712,961 A * | 7/1955 | Richardson .............. 239/105 |
| 3,029,295 A | 4/1962 | Thermet et al. |
| 3,062,899 A | 11/1962 | Sax |
| 3,141,860 A | 7/1964 | Sauer et al. |
| 3,192,272 A | 6/1965 | Asadorian |
| 3,232,959 A | 2/1966 | Hahn |
| 3,250,739 A | 5/1966 | Sauer et al. |
| 3,285,965 A | 11/1966 | Jenkner |
| 3,318,664 A * | 5/1967 | Latham, Jr. et al. ......... 423/455 |
| 3,331,797 A | 7/1967 | Kopetz et al. |
| 3,387,051 A | 6/1968 | Norell |
| 3,428,700 A | 2/1969 | Cyba |
| 3,578,716 A | 5/1971 | Robinson |
| 3,591,645 A | 7/1971 | Selwitz |
| 3,610,537 A * | 10/1971 | Nakagawa et al. ....... 239/419.3 |
| 3,658,634 A | 4/1972 | Yanagi et al. |
| 3,711,562 A | 1/1973 | Maui et al. |
| 3,711,563 A | 1/1973 | Carlson et al. |
| 3,733,366 A | 5/1973 | Burk |
| 3,752,856 A | 8/1973 | Nagy et al. |
| 3,760,003 A | 9/1973 | Asadorian et al. |
| 3,763,248 A | 10/1973 | Mitchell |
| 3,787,512 A | 1/1974 | Nelson |
| 3,833,674 A | 9/1974 | Brackenridge |
| 3,839,140 A | 10/1974 | Tyler et al. |
| 3,845,146 A | 10/1974 | Moore et al. |
| 3,875,249 A | 4/1975 | Nelson |
| 3,883,481 A | 5/1975 | Kopetz et al. |
| 3,899,466 A | 8/1975 | Dubeck et al. |
| 3,911,033 A | 10/1975 | Schaffner et al. |
| 3,931,081 A | 1/1976 | Dany et al. |
| 3,956,403 A | 5/1976 | Orlando et al. |
| 3,959,387 A | 5/1976 | Brackenridge |
| 3,965,197 A | 6/1976 | Stepniczka |
| 3,971,758 A | 7/1976 | Anderson et al. |
| 4,013,728 A | 3/1977 | Brackenridge |
| 4,067,930 A | 1/1978 | Versnel et al. |
| 4,130,605 A | 12/1978 | Barkhuff, Jr. |
| 4,143,081 A | 3/1979 | Carel et al. |
| 4,150,066 A | 4/1979 | Kudo et al. |
| 4,160,112 A | 7/1979 | Levek et al. |
| 4,214,103 A | 7/1980 | Garman et al. |
| 4,223,169 A | 9/1980 | Barda |
| 4,235,379 A * | 11/1980 | Beamer ...................... 239/230 |
| 4,279,808 A | 7/1981 | Hornbaker et al. |
| 4,287,373 A | 9/1981 | Garman et al. |
| 4,301,058 A | 11/1981 | Neukirchen et al. |
| 4,327,227 A | 4/1982 | Ayres et al. |
| 4,431,847 A | 2/1984 | Bossier et al. |
| 4,461,743 A * | 7/1984 | Chowdhury et al. ........ 422/129 |
| 4,521,633 A | 6/1985 | Pedjac |
| 4,546,139 A | 10/1985 | Bay et al. |
| 4,564,697 A | 1/1986 | Sutker |
| 4,569,596 A | 2/1986 | Romanchik et al. |
| 4,619,961 A | 10/1986 | Sutker et al. |
| 4,623,583 A | 11/1986 | Mischutin |
| 4,639,481 A | 1/1987 | Giles, Jr. |
| 4,639,486 A | 1/1987 | Liu |
| 4,659,021 A | 4/1987 | Bark et al. |
| 4,666,947 A | 5/1987 | Brichta et al. |
| 4,701,564 A | 10/1987 | Decaudin et al. |
| 4,716,251 A | 12/1987 | Scymanski et al. |
| 4,717,776 A | 1/1988 | Brackenridge et al. |
| RE32,606 E | 2/1988 | Stepniczka |
| 4,740,629 A | 4/1988 | Brackenridge et al. |
| 4,751,260 A | 6/1988 | Kress et al. |
| 4,766,253 A | 8/1988 | Rauber |
| 4,778,933 A | 10/1988 | McKinnie et al. |
| 4,814,525 A | 3/1989 | Rule et al. |
| 4,820,770 A | 4/1989 | Schleifstein |
| 4,849,547 A | 7/1989 | Stollar et al. |
| 4,857,597 A | 8/1989 | Schleifstein |
| 4,871,863 A | 10/1989 | Khuddus |
| 4,871,882 A | 10/1989 | Stollar et al. |
| 4,879,353 A | 11/1989 | Sanders et al. |
| 4,913,848 A | 4/1990 | Lee |
| 4,925,994 A | 5/1990 | Mais et al. |
| 4,929,775 A | 5/1990 | Hussain |
| 4,929,785 A | 5/1990 | Hussain |
| 4,957,958 A | 9/1990 | Schleifstein |
| 4,959,500 A | 9/1990 | Schleifstein |
| 4,981,890 A | 1/1991 | Schleifstein |
| 4,983,781 A | 1/1991 | Desmurs et al. |
| 4,990,707 A | 2/1991 | Mais et al. |
| 5,003,117 A | 3/1991 | Hussain |
| 5,004,847 A | 4/1991 | Beaver et al. |
| 5,004,848 A | 4/1991 | Beaver et al. |
| 5,008,425 A | 4/1991 | Stahly |
| 5,008,477 A | 4/1991 | Hussain |
| 5,017,728 A | 5/1991 | McKinnie et al. |
| 5,030,778 A | 7/1991 | Ransford |
| 5,036,126 A | 7/1991 | Rinehart et al. |
| 5,039,729 A | 8/1991 | Brackenridge et al. |
| 5,041,687 A | 8/1991 | McKinnie et al. |
| 5,049,601 A | 9/1991 | Khuddus |
| 5,053,447 A | 10/1991 | Hussain |
| 5,055,235 A | 10/1991 | Brackenridge et al. |
| 5,059,650 A | 10/1991 | Goettsch et al. |
| 5,077,334 A | 12/1991 | Hussain |
| 5,077,444 A | 12/1991 | Cook, Jr. et al. |
| 5,107,035 A | 4/1992 | Hines et al. |
| 5,116,898 A | 5/1992 | Schleifstein |
| 5,124,496 A | 6/1992 | Templeton et al. |
| 5,136,107 A | 8/1992 | Stephens et al. |
| 5,208,389 A | 5/1993 | McKinnie et al. |
| 5,210,321 A | 5/1993 | McKinnie et al. |
| 5,218,017 A | 6/1993 | Doucet et al. |
| 5,237,112 A | 8/1993 | LaRose |
| 5,246,601 A | 9/1993 | Jensen |
| 5,281,648 A | 1/1994 | Doucet et al. |
| 5,283,375 A | 2/1994 | McKinnie et al. |
| 5,302,768 A | 4/1994 | Hussain |
| 5,324,874 A | 6/1994 | Ransford et al. |
| 5,387,636 A | 2/1995 | Landry et al. |
| 5,401,890 A | 3/1995 | Parks |
| 5,457,248 A | 10/1995 | Mack et al. |
| 5,527,971 A | 6/1996 | McKinnie |
| 5,593,619 A | 1/1997 | Bottelberghe et al. |
| 5,674,972 A | 10/1997 | Wabeeke et al. |
| 5,677,390 A | 10/1997 | Dadgar et al. |
| 5,686,538 A | 11/1997 | Balhoff et al. |
| 5,710,354 A | 1/1998 | Hussain |
| 5,723,690 A | 3/1998 | McKinnie |
| 5,741,949 A | 4/1998 | Mack |
| 5,744,659 A | 4/1998 | Tsuda et al. |
| 5,760,161 A | 6/1998 | Goins, Jr. et al. |
| 5,767,203 A | 6/1998 | Ao et al. |
| 5,824,241 A | 10/1998 | Horvat |
| 5,847,232 A | 12/1998 | McKinnie |
| 5,852,131 A | 12/1998 | Balhoff et al. |
| 5,852,132 A | 12/1998 | Dadgar et al. |
| 5,916,978 A | 6/1999 | Ao et al. |
| 5,965,731 A | 10/1999 | Ao et al. |
| 6,002,050 A | 12/1999 | McKinnie |
| 6,063,852 A | 5/2000 | Hussain |
| 6,084,136 A | 7/2000 | Holub et al. |
| 6,084,137 A | 7/2000 | McKinnie et al. |
| 6,117,371 A | 9/2000 | Mack |
| 6,147,264 A | 11/2000 | Manimaran et al. |
| 6,162,953 A | 12/2000 | McKinnie et al. |
| 6,207,765 B1 | 3/2001 | Ao et al. |
| 6,218,584 B1 | 4/2001 | Manimaran et al. |

|               |        |                  |
|---------------|--------|------------------|
| 6,232,393 B1  | 5/2001 | Dadgar et al.    |
| 6,232,408 B1  | 5/2001 | Dadgar et al.    |
| 6,235,831 B1  | 5/2001 | Reed et al.      |
| 6,235,844 B1  | 5/2001 | Dadgar et al.    |
| 6,235,946 B1  | 5/2001 | Manimaran et al. |
| 6,518,468 B1  | 2/2003 | Parks et al.     |
| 2001/0047118 A1 | 11/2001 | Parks et al.  |

FOREIGN PATENT DOCUMENTS

|    |                |         |
|----|----------------|---------|
| EP | 0347116 B1     | 12/1989 |
| EP | 0445595 A2     | 9/1991  |
| EP | 0460922 B1     | 12/1991 |
| EP | 0489406 A1     | 6/1992  |
| EP | 0502333 A1     | 9/1992  |
| EP | 0571859 A2     | 1/1993  |
| EP | 0527493 A1     | 2/1993  |
| GB | 918723         | 2/1963  |
| GB | 981833         | 1/1965  |
| GB | 991067         | 5/1965  |
| GB | 1411524        | 10/1975 |
| GB | 1472383        | 5/1977  |
| GB | 1572659        | 7/1980  |
| JP | 54044623       | 4/1979  |
| JP | 61040232 A *   | 2/1986  |
| WO | WO 91/13915    | 9/1991  |
| WO | WO 94/22978    | 10/1994 |
| WO | WO 96/08457    | 3/1996  |
| WO | WO 96/15087    | 5/1996  |

OTHER PUBLICATIONS

Butin, K.B., et al., "A Stufy of Reaction Conditions for the Reaction of Polybromobenzyl Bromides and Other Benzyl Bromides with Mettalic Mercury", 1985, 8 pages.

Horng, D.N., et al., "Photcatalytic Oxidation of Aromatic Compounds in Titanium Dioxide Suspension", Dep. Phy. Chem., Mil. Acad. Kaohsiun, Taiwan (1990), 5 pages.

Sydnes, L.K., et al., "Photochemical Oxidation of toluene and Xylenes. Concurrent Formation of Products . . . ", Dep. Chem. Univ. Tromso, Norway (1985) Abstract—2 pages.

Butin, K.P., et al., "Study of Conditions for the Reactions of Polybromodebenzyl Bromides and Some Other Benzyl Bromines with Mercury Metal", Univ. of Moscow, 1985, Abstract.

* cited by examiner

METHOD AND APPARATUS FOR PRODUCING DECABROMODIPHENYL ALKANES

This application is a divisional application of and claims the benefit of U.S. patent application Ser. No. 10/323,012 filed on Dec. 18, 2002, now U.S. Pat. No. 6,841,707, and claims the benefit of U.S. Provisional Patent Application Ser. No. 60/345,063 filed Dec. 21, 2001, the complete disclosures of which are hereby expressly incorporated by reference.

BACKGROUND OF THE INVENTION

1. Field of the Invention

This invention relates to methods and an apparatus for producing decabromodiphenyl alkanes. More specifically, the field of the invention is that of producing decabromodiphenyl ethane.

2. Description of the Related Art

Halogenated aromatic compounds are often employed as flame retardant agents. Flame retardants are substances applied to or incorporated into a combustible material to reduce or eliminate its tendency to ignite when exposed to a low-energy flame, e.g., a match or a cigarette. The incorporation of flame retardants into the manufacture of electronic equipment, upholstered furniture, construction materials, textiles and numerous other products is well known.

Brominated aromatic compounds are often utilized as flame retardant agents in polymer compositions such as the outer housing of computers, television sets, and other electronic appliances. One group of halogenated flame retardants are decabromodiphenyl alkanes. The manufacture of decabromodiphenyl alkanes is known. Conventionally, decabromodiphenyl alkanes are prepared by reacting a diphenyl alkane with bromine in the presence of a bromination catalyst, such as $AlCl_3$ or $FeCl_3$.

For example, U.S. Pat. No. 5,030,778 to Ransford discloses a process for producing decabromodiphenyl alkanes in which bromine and a bromination catalyst are charged to a reaction vessel. Liquid diphenyl alkane is fed by a dip tube into the reaction vessel at a point which is beneath the level of the charged liquid bromine and catalyst. The stated advantages of this sub-surface addition method are that (1) a product with a high average bromine number is obtained faster when the diphenyl alkane is fed below the surface of the charged liquid bromine and catalyst; and (2) splattering of the reaction mass associated with the addition of the diphenyl alkane into the vessel is reduced.

One disadvantage to adding the diphenyl alkane to the vessel at a location below the surface of the charged bromine and catalyst is that the dip tubes used for adding the diphenyl alkane to the vessel are prone to plugging. It is believed that the sub-surface addition dip tubes become plugged when a small amount of diphenyl alkane remains at the tip of the tube and reacts in place, thereby forming insoluble, high melting point material. It is believed that this is more likely to occur at the end of the addition or if the diphenyl alkane addition is interrupted. This susceptibility to plugging prevents the manufacturer from being able to stop and start the diphenyl alkane addition, which is sometimes desirable for controlling the evolution HBr gas.

It is also believed that the agitation of the reaction mass may create a vortex within the tip of the sub-surface addition dip tube. This vortex may pull solids from the reaction mass into the tube, thereby creating a blockage. Additionally, because some diphenyl alkanes, such diphenylethane ("DPE"), are solids at room temperature and are fed to the reaction vessel as liquids, they may begin to crystallize in an unheated dip tube if the feed is interrupted for any reason. In the event that the sub-surface dip tube does become plugged, regardless of the reason, the diphenyl alkane feed must be stopped and the tube must be pulled out of the reactor in order to remove the blockage. It is desirable to avoid the need to remove the dip tube, as the vapor space of the reaction vessel is filled with toxic and corrosive bromine vapors which may escape during removal.

The above-surface diphenyl alkane addition technique of the present invention reduces dip tube plugging, thereby providing a more efficient method of adding diphenyl alkane to a reactor charged with bromine and catalyst.

SUMMARY OF THE INVENTION

The present invention is directed to a method and apparatus for producing decabromodiphenyl alkanes, particularly decabromodiphenylethane. In one embodiment of the invention, a diphenyl alkane, such as diphenylethane, is fed into a reaction vessel containing liquid bromine and a bromination catalyst via a dip tube located above the surface level of the charged liquid bromine and catalyst. The DPE may be fed to the reaction vessel under pressure and at a relatively high velocity from a point above the level of the bromine and catalyst in the reaction vessel.

Another method for preparing decabromodiphenyl alkanes according to the present invention includes the steps of charging a reaction vessel with bromine and a bromination catalyst, providing a dip tube apparatus having a first end and a second end located in the reaction vessel above the surface level of the bromine and the bromination catalyst, introducing diphenyl alkane through the dip tube apparatus such that the diphenyl alkane flows from the first end, to the second end and enters the reaction vessel at a point above the surface level of the bromine and bromination catalyst in the reaction vessel, reacting the diphenyl alkane with the bromine and the bromination catalyst thereby forming a reaction mass, and recirculating the reaction mass through the dip tube apparatus so as to form a curtain of recirculated reaction mass around the diphenyl alkane being introduced into the reaction vessel. An excess of bromine above that needed to brominate the diphenyl alkane to the desired degree is utilized.

In accordance with the present invention, the crude decabromodiphenyl alkane, such as decabromodiphenylethane, obtained by the aforementioned process is isolated and purified. Any one of numerous known isolation and purification methods may be utilized. For example, the solid may be isolated through direct removal from the slurry by filtration or centrifugation. The solid decabromodiphenyl alkane could as be removed by combining the reaction mass with water and striping the bromine through the use of heat and/or a vacuum. In one method of the invention, the crude decabromodiphenyl alkane is first made into a water slurry, and is transferred to a another reactor. The slurry is washed with an alkaline solution and the solid decabromodiphenyl alkane is separated and washed with water. The solid decabromodiphenyl alkane is then in the form of a filter cake. The filter cake may be treated in any one of a number of known ways. For example, the cake may first be dried and then fractured and/or heat treated in a number of ways. The wet decabromodiphenyl alkane product may also be treated without first drying, as disclosed in U.S. Pat. No. 4,659,021 to Bark, et al. In one embodiment of the present invention, the filter cake is dried and then ground twice in an air mill using air which is heated to an inlet temperature of approximately 260° C. The ground decabromodiphenyl alkane is then heat-treated at approximately 240°

C. for three to four hours in order to release any free bromine which may be present in the product. The release of free bromine improves the purity and the color of the end product. Other known isolation and purification methods may also be utilized, such as those disclosed in U.S. Pat. No. 4,327,227 to Ayres, et al. and U.S. Pat. No. 5,030,778 to Ransford.

An apparatus for preparing decabromodiphenyl alkanes according to the present invention includes a dip tube apparatus disposed above the surface level of the charged liquid bromine in the reaction vessel and includes an inner tube and an outer tube. The inner tube has a first end and a second end. The first end is adapted to receive a flow of diphenyl alkane. The second end of the inner tube is adapted to receive a plug. The plug includes a hollow portion and an opening. When the inner tube and the plug are engaged, the plug and the inner tube are in fluid communication with one another. The diphenyl alkane flows through the inner tube, through an opening in the plug, and into the reaction vessel at a location which is above the surface level of the charged liquid bromine and the bromination catalyst. Plugs having a variety of opening sizes and configurations may be chosen in order to achieve the desired flow rate diphenyl alkane. Alternatively, the plug can be eliminated and the opening through which the diphenyl alkane flows can be formed in one end of the inner tube.

The outer tube of the dip tube apparatus extends around the inner tube. The reaction mass within the reaction vessel is pumped out of the reaction vessel, through the outer tube, and then back into the reaction vessel. The outer tube is spaced from the inner tube, such that the recirculated reaction mass re-enters the reaction vessel in the form of a curtain surrounding the diphenyl alkane stream. The curtain of recirculated reaction mass does not come into contact with the stream of diphenyl alkane being simultaneously added to the reaction vessel through the inner tube.

Other features of the present invention will be apparent to those of skill in the art from the following detailed description and the accompanying drawings.

BRIEF DESCRIPTION OF THE DRAWINGS

Corresponding reference characters indicate corresponding parts throughout the several views. The examples set out herein illustrate a preferred embodiment of the invention, in one form, and are not to be construed as limiting the scope of the invention is any manner.

DETAILED DESCRIPTION OF THE INVENTION

Figure 1:
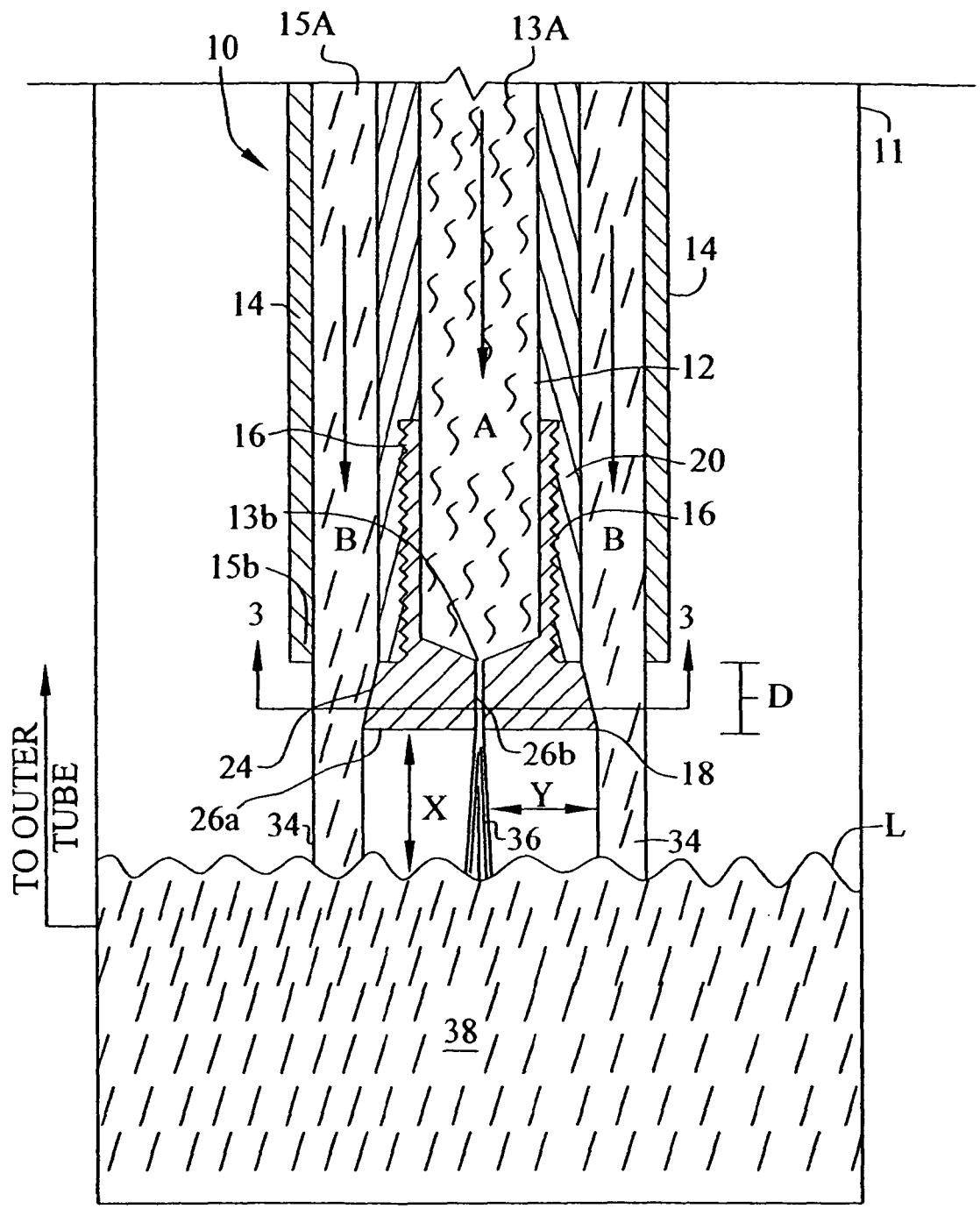
FIG. 1 is a sectional view illustrating the dip tube apparatus according to one embodiment of the present invention disposed in a reaction vessel.

With reference to FIG. 1, dip tube apparatus 10 is disposed in reaction vessel 11. Reaction vessel 11 may be any size desired, but for commercial applications, a reactor of at least 3,000 gallons is typically preferred.

Dip tube apparatus 10 includes inner tube 12 and outer tube 14. Inner tube 12 may be manufactured out of Teflon® (polytetrafluoroethylene) or any other suitable material having similar properties, and outer tube 14 may be manufactured of Kynar® (polyvinylidene fluoride) or any other suitable material having similar properties. Inner tube 12 includes first end 13a and second end 13b. First end 13a is adapted for receiving a flow of a diphenyl alkane, such as, for example, DPE, as indicated by arrow A. Second end 13b is adapted for receiving plug 18, as described below.

Figure 3:
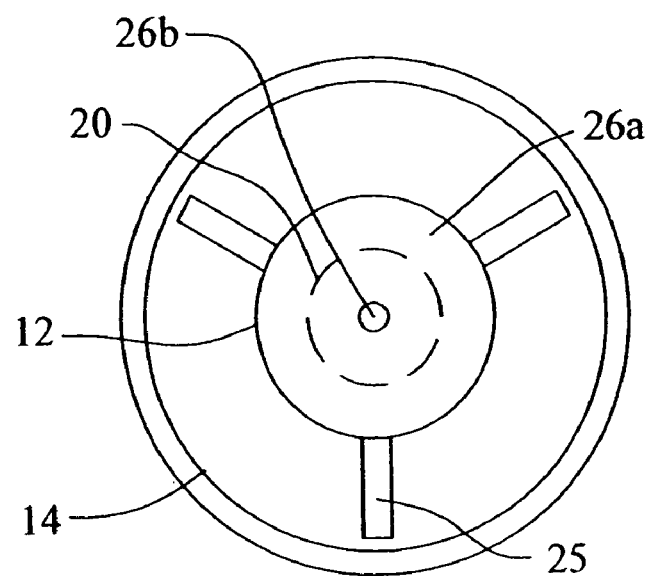
FIG. 3 is an end view of the dip tube apparatus taken along line 3-3 of FIG. 1.

Outer tube 14 extends along and surrounds inner tube 12 as shown. Outer tube 14 includes first end 15a and second end 15b. FIG. 3 illustrates an end view of dip tube apparatus 10 taken along line 3-3 of FIG. 1. As shown in FIG. 3, spacers 25 serve to separate inner tube 12 from outer tube 14. Spacers 25 are may be manufactured from a 15% glass Teflon® material or any other suitable material.

Figure 2:
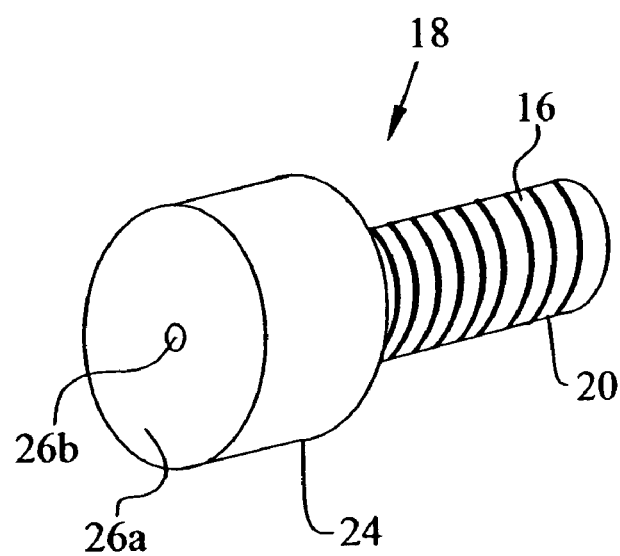
FIG. 2 is a perspective views of a plug that is a component of the dip tube apparatus of FIG. 1.

With reference to FIG. 2, plug 18, in the embodiment shown, includes a hollow portion 20 and a generally disc-shaped portion 24. Disc-shaped portion 24 includes a first surface 26a having an opening 26b therein. Note that in the embodiment shown, the side of disc-shaped portion 24 is flared. Hollow portion 20 and opening 26b are in fluid communication such that DPE flowing through hollow portion 20 will exit plug 18 through opening 26b. The size and shape of opening 26b may be varied depending upon the desired flow rate of DPE into reaction vessel 11. Typically, opening 26b will have a diameter of between about 0.0625" and about 0.0937". In the embodiment shown, second end 13b of inner tube 12 includes a threaded portion 16 which is adapted to receive corresponding threads 16 of plug 18 such that plug 18 is secured within second end 13b of inner tube 12. This arrangement allows the size and shape of opening 26b to be changed by changing plug 18. Other mechanisms for securing plug 18 to inner tube 12 may also be utilized. When plug 18 is secured within second end 13b of inner tube 12, inner tube 12 and plug 18 are in fluid communication such DPE flowing through inner tube 12 will flow into hollow portion 20 and out opening 26b. Plug 18 may be manufactured from Teflon® or any other suitable material.

Note that plug 18 can be completely eliminated by constructing second end 13b of inner tube 12 with an appropriately sized and shaped opening for introducing DPE into reaction vessel 11. Of course, this would mean that the entire inner tube 12 would have to be changed to change the size and shape of the opening.

In the embodiment shown in FIG. 1, dip tube apparatus 10 is disposed in reaction vessel 11 such that second end 15b of outer tube 14 is located at the same level as second end 13 of inner tube 12. Both second end 15b of outer tube 14 and second end 13b of inner tube 12 are located a distance D above surface 26a of plug 18. In the embodiment shown, distance D corresponds to the thickness of portion 24 of plug 18. In one embodiment of the invention, distance D is about 0.5 inches. Note also that it is not necessary that surface 26a of plug 18 be located below second end 15b of outer tube 14. That is, inner tube 12 and plug 18 may be positioned such that surface 26a is recessed within outer tube 14 and is located further from level L than is second end 15b of outer tube 14. As further shown in FIG. 1, surface 26a of plug 18 is located a distance X above surface level L of the charged bromine and catalyst. In one embodiment of the invention, distance X is about 4 inches. Typically, distance X will be between about 1 inch and about 12 inches.

If an inner tube 12 is utilized without a plug 18, as described above, inner tube 12 and outer tube 14 would be positioned such that second end 13b of inner tube 12 is located a distance D below second end 15b of outer tube 14. Similarly, inner tube 12 would be positioned such that second end 13b is located a distance X above level L.

In use, DPE is fed, under pressure, through inner tube 12 and emitted as a stream 36 via opening 26a into reaction vessel 11. The DPE preferably has a purity level of about 99.7% or greater, however, DPE of different purity levels can be used depending on the desired characteristics of the final product. The pressure at which the DPE is fed is preferably at least about 20 psig and preferably between about 20 psig and about 60 psig. The DPE stream 36 preferably has a velocity within the range of about 9 meters per second to about 25 meters per second. In one embodiment of the invention, the DPE is fed at about 17.5 meters per second under a pressure of about 30 psig. An agitator (not shown) operating at approximately 47-88 rpm and disposed within reaction vessel 11 mixes the DPE and the bromine reaction medium, thereby facilitating the reaction.

As the DPE is added to reaction vessel 11, the reaction mass 38 is recirculated to first end 15a of outer tube 14 and allowed to flow through outer tube 14 (shown in FIG. 1 by arrows B), along inner tube 12 and back into reaction vessel 11. Preferably, reaction mass 38 is recirculated at a rate of between about 45 gallons per minute to 250 gallons per minute. In this manner, a curtain 34 of reaction mass 38 is formed around DPE stream 36. The distance Y between curtain 34 and DPE stream 26 is preferably at least about 0.5 inches. In one embodiment of the invention, distance Y is about 0.867". Note that DPE stream 26 does not come into contact with curtain 34. The flared sides of portion 24 of plug 18 assists in keeping the DPE stream 26 and the curtain 34 separated. Note that any portion of reaction mass 38 that splashes as a result of the DPE feed will be contained by curtain 34 and carried back into the remainder of the reaction mass 38.

Decabromodiphenylethane may be obtained according to the present invention by reacting DPE in the presence of an excess of bromine and a bromination catalyst. The molar ratio of bromine to DPE is between about 18:1 and about 50:1. Preferably, the ratio is between about 18:1 to about 39:1. Appropriate bromination catalysts include aluminum halides, such as aluminum chloride and aluminum bromide, as well as iron powder. Other catalysts may also be used.

During the DPE addition, the temperature of the reaction mass is preferably in the range of about 50° C. to about 60° C. Preferably the temperature of the reaction mass is maintained at 55° C. until the DPE feed is complete. The temperature is then increased to approximately 60° C. and held constant for the duration of the reaction time. The reaction time will vary depending upon the amount of DPE being added, and upon the rate at which the DPE is added. For commercial production, reaction times will likely be between three and six hours.

As noted above, isolation and purification of the resulting decabromodiphenylethane may be carried out in a variety of ways. In one method, the decabromodiphenylethane slurry is placed in a pressurized vessel charged with water which has been heated to approximately 70° C. Once the slurry addition is complete, the temperature within the vessel is increased to approximately 100° C. to facilitate the removal of any remaining free bromine. The water slurry is transferred to a tank which is charged with a solution which is 25% alkaline. The resulting slurry is then fed to a centrifuge where the solid decabromodiphenylethane product is separated and washed with water. The solid is in the form of a filter cake. The filter cake of decabromodiphenylethane is then dried and ground twice in an air mill using air heated to an inlet temperature of approximately 260° C. The resulting material is heat-treated at approximately 240° C. for 3-4 hours. The final product preferably has a yellowness index of below about 10, and more preferably below about 9.

EXAMPLE

A 3000 gallon glass lined Pfaudler reactor was equipped with a vertical H-type baffle, condenser system, 41" Pfaudler Cryo-lock reverse curve agitator, temperature sensor, and the dip tube apparatus described above. 21,210 kg (132,278.41 moles) of liquid bromine and 63.5 kg (476.26 moles) of aluminum chloride were charged to the reaction vessel. The agitator was then turned on and ranged in speed from 47 to 88 rpm. The reactor was heated to 55° C. 618 kg (3395.6 moles) of DPE was then charged through the dip tube, as described above, at a rate of 4-8.5 lbs./min. The DPE addition ranged from 3.5 to 5 hours. Once the feed was completed, the reaction temperature was increase to 60° C. and held at that temperature for thirty minutes.

A 4000 gallon glass lined Pfaudler reactor was equipped with a vertical H-type baffle, condenser system, 41" Pfaudler Cryo-lock reverse curve agitator, and temperature sensor. The vessel was charged with 1850 gallons of water. The water was then heated to 70° C. The bromine slurry from the reactor was fed into the vessel over a 2.5 to 3 hour period, while maintaining 5 to 5.5 lbs. of pressure within the vessel. Once the slurry addition was complete, the temperature within the vessel was raised to 100° C. to complete the bromine removal.

The water slurry was transferred to a 5000 gallon tank equipped with an agitator. The tank was charged with 475 gallons of a 25% caustic (alkaline) solution. The resulting slurry was then fed to a centrifuge where the solid was separated and washed with water. The filter cake was then dried. The resulting material was then ground twice by passing it through a Fluid Energy Aljet air mill using air heated to 260° C. The product was then heat treated in a Wyssmont drier at 240° C. for 3 to 4 hours.

The conditions and results of the reactions run are illustrated in the following table. Note that some of the reactions were run without utilizing the curtain of recirculated reaction mass. In these runs, the DPE was simply fed under pressure to the reaction vessel at a point above the level of the bromine and bromination catalyst.

| Run # | Agitation Rate RPM | Hole Diameter (inches) | Bromine Weight (rcyl) lbs. | Bromine Weight (vir) lbs. | Bromine temp initial ° C. | Bromine temp final ° C. | DPE Assay % | DPE Rate lbs/min | DPE Weight total lbs. | DPE Linear Feed Rate m/sec | Wet cake GC Assay % |
|---|---|---|---|---|---|---|---|---|---|---|---|
| Above Surface | | | | | | | | | | | |
| 20 | 88 | 0.0625 | 23360 | 23360 | 56.7 | 54.2 | 98.7 | 4.62 | 1363 | 17.7 | 99.07 |
| 21 | 88 | 0.0937 | 47510 | 0 | 53.3 | 53.3 | 98.7 | 5.4 | 1363 | 9.2 | 98.93 |
| 22 | 88 | 0.07813 | 37360 | 9340 | 58.3 | 51.7 | 98.7 | 4.4 | 767 | 10.8 | 98.82 |
| 23 | 88 | 0.07813 | 46700 | 0 | 57.8 | 53.3 | 98.7 | 10 | 640 | 24.5 | 98.7 |
| 24 | 88 | 0.07813 | 46710 | 0 | 57.2 | 57.2 | 98.7 | 4.3 | 741 | 10.5 | |
| 25 | | 0.07813 | 46710 | 0 | 56.7 | | 98.7 | | 463 | 0.0 | |

-continued

| Run # | Agitation Rate RPM | Hole Diameter (inches) | Bromine Weight (rcyl) lbs. | Bromine Weight (vir) lbs. | Bromine temp initial °C. | Bromine temp final °C. | DPE Assay % | DPE Rate lbs/min | DPE Weight total lbs. | DPE Linear Feed Rate m/sec | Wet cake GC Assay % |
|---|---|---|---|---|---|---|---|---|---|---|---|
| | | | | | Above surface curtain | | | | | | |
| 26 | 75 | 0.07813 | 46710 | 0 | 56.7 | 55.6 | 98.7 | 5 | 1363 | 12.2 | 99.102 |
| 27 | 75 | 0.07813 | 46720 | 0 | 55.0 | 56.1 | 98.7 | 5.05 | 1363 | 12.4 | 99.05 |
| 28 | 75 | 0.07813 | 43280 | 0 | 56.7 | 58.3 | 98.7 | 4.99 | 1263 | 12.2 | 99.24 |
| 29 | 46 | 0.07813 | 43340 | 0 | 59.2 | 57.3 | 98.7 | 5.3 | 1263 | 13.0 | 99.14 |
| 30 | 46 | 0.07813 | 43321 | 0 | | | 98.7 | | 1263 | 0.0 | 98.83 |
| 31 | 47 | 0.07813 | 46710 | 0 | | | 98.7 | | 1338 | 0.0 | 99.18 |
| 32 | 47 | 0.07813 | 45110 | 0 | 59.2 | 56.4 | 98.7 | 5.4 | 1315 | 13.2 | 98.98 |
| 33 | 47 | 0.07813 | 45100 | 0 | 56.1 | 56.7 | 98.7 | 4.7 | 326 | 11.5 | 98.8 |
| 34 | 47 | 0.07813 | 45100 | 0 | 56.1 | 57.8 | 98.7 | 5.89 | 1315 | 14.4 | 99.01 |
| 35 | 47 | 0.0625 | 45120 | 0 | 55.9 | 56.6 | 98.7 | 5 | 1315 | 19.1 | 99.08 |
| 36 | 47 | 0.07813 | 46660 | 0 | 58.9 | 57.8 | 98.7 | 5.37 | 1315 | 13.1 | 99.2 |
| 37 | 47 | 0.07813 | 46730 | 0 | 56.5 | | 98.7 | | 1773 | 0.0 | 98.6 |
| 38 | 47 | 0.07813 | | | | | 98.7 | | | 0.0 | 99.27 |

While this invention has been described with reference to specific embodiments, the present invention may be further modified within the spirit and scope of the disclosure. This application covers such departures from the present disclosure as come within the known or customary practice in the art to which the invention pertains and which fall within the limits of the appended claims.

What is claimed is:

1. An apparatus comprising:
   a dip tube apparatus within a reaction vessel comprising bromine and catalyst, the dip tube apparatus comprising a first and second tube;
   the first tube having a first end and a second end, the second end being located at a point above the surface level of the bromine and catalyst;
   the second tube surrounding the first tube, the second tube having a first end and a second end, the second end being located at a point above the surface level of the bromine and catalyst,
   a fluid connection between an outlet of said reaction vessel and an inlet at the first end of the second tube; and
   a plug in said first tube having an opening through which diphenyl alkane flows into the reaction vessel, said plug separating the diphenyl alkane stream from a curtain of recirculated reaction mass formed by said second tube.

2. The apparatus of claim 1, wherein the plug is connected to the second end of the first tube.

3. The apparatus of claim 2, wherein the plug is located above the surface level of the bromine and catalyst.

4. The apparatus of claim 2, wherein the plug is removable from the second end of the first tube.

5. The apparatus of claim 2, wherein the plug includes a flared portion.

6. The apparatus of claim 1, further including a plurality of interchangeable plugs having different sized openings.

7. The apparatus of claim 1, further including a plurality of interchangeable plugs having different shaped openings.

8. The apparatus of claim 1, further including at least one spacer positioning the first tube within the second tube.

9. The apparatus of claim 2, wherein the second end of the second tube is located farther above the surface level of the bromine and catalyst than is the second end of the first tube.

10. The apparatus of claim 1, wherein the opening of the plug is configured to provide the diphenyl alkane stream at a velocity of from about 9 meters per second to about 25 meters per second.

* * * * *